(12) United States Patent
Fu et al.

(10) Patent No.: US 11,464,446 B2
(45) Date of Patent: Oct. 11, 2022

(54) PHYSIOLOGICAL STATUS MONITORING APPARATUS AND METHOD

(71) Applicant: MEDIATEK INC., Hsin-Chu (TW)

(72) Inventors: Chih-Ming Fu, Hsin-Chu (TW); Hung-Chih Chiu, Hsin-Chu (TW)

(73) Assignee: MEDIATEK INC., Hsin-Chu (TW)

( * ) Notice: Subject to any disclaimer, the term of this patent is extended or adjusted under 35 U.S.C. 154(b) by 274 days.

(21) Appl. No.: 16/386,367

(22) Filed: Apr. 17, 2019

(65) Prior Publication Data
US 2020/0330030 A1 Oct. 22, 2020

(51) Int. Cl.
| A61B 5/113 | (2006.01) |
| A61B 5/00 | (2006.01) |
| A61B 5/0205 | (2006.01) |
| A61B 5/024 | (2006.01) |
| H04W 4/38 | (2018.01) |

(52) U.S. Cl.
CPC .......... *A61B 5/4818* (2013.01); *A61B 5/0205* (2013.01); *A61B 5/113* (2013.01); *A61B 5/681* (2013.01); *A61B 5/7203* (2013.01); *A61B 5/7275* (2013.01); *A61B 5/742* (2013.01); *A61B 5/02416* (2013.01); *H04W 4/38* (2018.02)

(58) Field of Classification Search
CPC ....... A61B 5/48; A61B 5/4806; A61B 5/4809; A61B 5/4812; A61B 5/4815; A61B 5/4818; A61B 5/11; A61B 5/1114; A61B 5/1118; A61B 5/113; A61B 5/1135; A61B 5/72; A61B 5/7203; A61B 5/721; A61B 5/7221; A61B 5/7225; A61B 5/7275; A61B 5/0205; A61B 5/02416; A61B 5/02438; A61B 5/68; A61B 5/6801; A61B 5/6802; A61B 5/681
USPC ........ 600/301, 322, 323, 843, 848, 529, 534
See application file for complete search history.

(56) References Cited

U.S. PATENT DOCUMENTS

| 7,572,225 | B2* | 8/2009 | Stahmann ................ A61B 5/00 600/300 |
| 9,826,911 | B2* | 11/2017 | Fu ....................... A61B 5/02405 |
| 11,000,223 | B2* | 5/2021 | Ser ........................ A61B 5/4818 |
| 11,241,173 | B2* | 2/2022 | Ting ........................ A61B 5/11 |
| 2005/0042589 | A1* | 2/2005 | Hatlestad .............. A61B 5/0031 434/262 |
| 2010/0152600 | A1* | 6/2010 | Droitcour ............. A61B 5/1114 600/534 |
| 2016/0270718 | A1 | 9/2016 | Heneghan et al. |
| 2018/0132789 | A1 | 5/2018 | Chen et al. |

FOREIGN PATENT DOCUMENTS

| CN | 109620208 A | 4/2019 |
| TW | 201528198 A | 7/2015 |
| TW | 201742596 A | 12/2017 |

* cited by examiner

*Primary Examiner* — Ahmed M Farah
(74) *Attorney, Agent, or Firm* — McClure, Qualey & Rodack, LLP

(57) ABSTRACT

A physiological status monitoring apparatus is provided. The physiological status monitoring apparatus comprises a motion sensor, an event detector, and an estimator. The motion sensor senses movement of an object to generate a sensing signal. The event detector detects abnormal events occurring on the object according to the sensing signal. The estimator outputs an index according to at least one abnormal event which occurs during a predetermined time period to indicate a possibility of pauses in breathing.

9 Claims, 12 Drawing Sheets

PHYSIOLOGICAL STATUS MONITORING APPARATUS AND METHOD

BACKGROUND OF THE INVENTION

Field of the Invention

The invention relates to a physiological status monitoring apparatus, and more particularly to a monitoring apparatus for detecting sleep apnea.

Description of the Related Art

Sleep apnea is a sleep disorder characterized by pauses in breathing or periods of shallow breathing during sleep. Each of pauses in breathing can last for a few seconds to a few minutes, and they happen many times a night. In the most common form, this follows loud snoring. There may be a choking or snorting sound as breathing resumes. As the disorder disrupts normal sleep, those affected may experience sleepiness or feel tired during the day. Sleep apnea monitoring devices currently in use includes a polysomnography (PSG) device. The PSG device includes many sensors that are in contact with or worn by a patient through leads, such as an electrocardiography (ECG) sensor, an electroencephalograph (EEG) sensor, an electromyography (EMG) sensor, a photoplethysmogram (PPG) sensor, a nasal pressure sensor, a piezoelectric sensor disposed on a chest band etc., which results in a poor sleep state of the patient during monitoring and, thus, affects monitoring results disadvantageously. In addition, the PSG device has a large volume and an expensive price, so it only operates in a hospital or sleep disorders center. Many in-home devices for monitoring sleep apnea are also provided, such as Apnea Risk Evaluation System (ARES™) equipped with an EEG sensor and a nasal/oral airflow detector and Watch PAT equipped with an Oxygen saturation and pulse detector. However, since the electrodes or patches of the above sensors/detectors may be not in good contact with the patient, the above devices have low signal quality.

BRIEF SUMMARY OF THE INVENTION

An exemplary embodiment of a physiological status monitoring apparatus is provided. The physiological status monitoring apparatus comprises a motion sensor, an event detector, and an estimator. The motion sensor senses movement of an object to generate a sensing signal. The event detector detects abnormal events occurring on the object according to the sensing signal. The estimator outputs an index according to at least one abnormal event which occurs during a predetermined time period to indicate a possibility of pauses in breathing.

An exemplary embodiment of a physiological status monitoring method is provided. The physiological status monitoring method comprises steps of sensing movement of an object to generate a sensing signal; detecting abnormal events occurring on the object according to the sensing signal; and outputting an index according to at least one abnormal event which occurs during a predetermined time period to indicate a possibility of pauses in breathing.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated model of carrying out the invention. This description is made for the purpose of illustrating the general principles of the invention and should not be taken in a limiting sense. The scope of the invention is best determined by reference to the appended claims.

Figure 1:
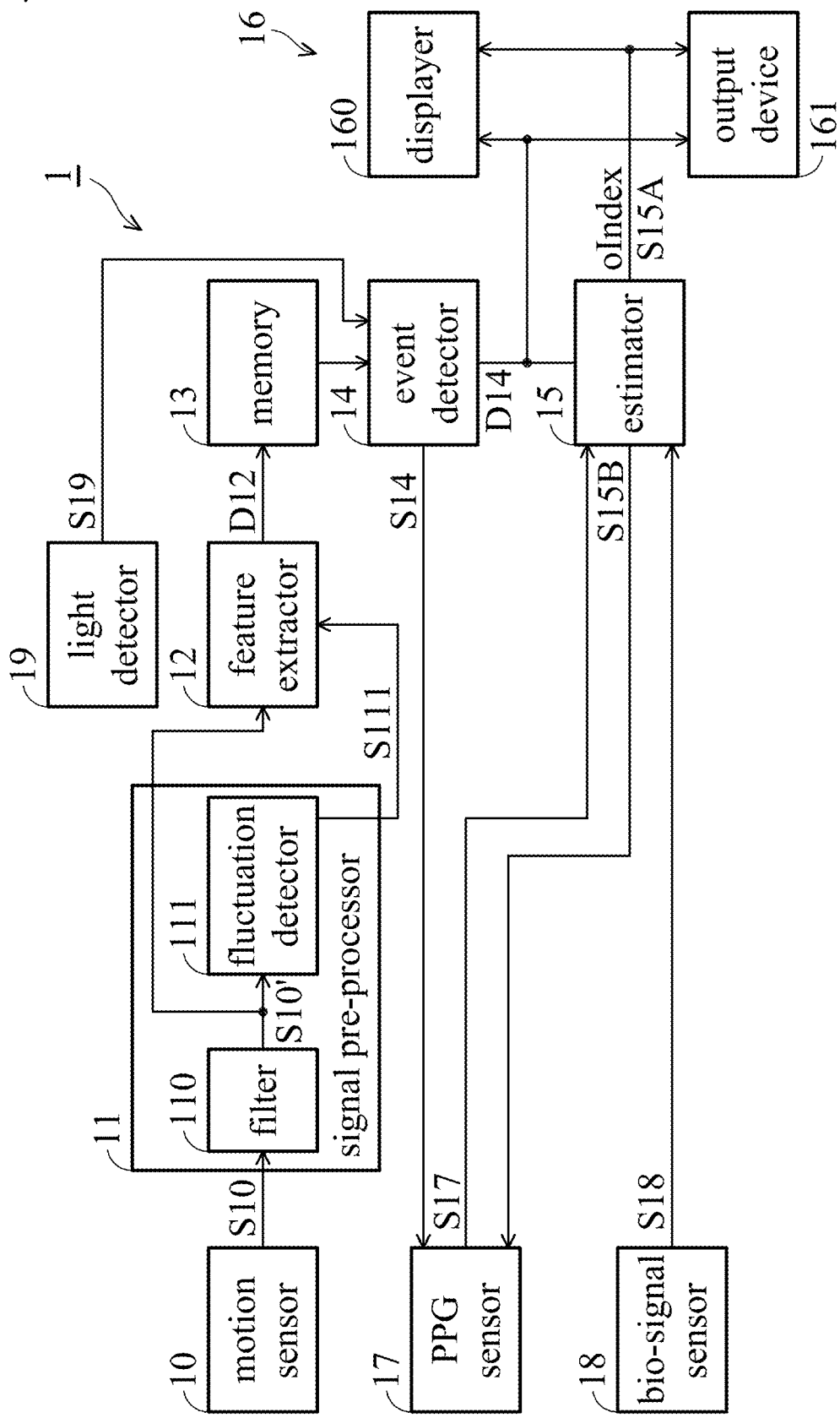
FIG. 1 shows one exemplary embodiment of a physiological status monitoring apparatus.
Figure 2:
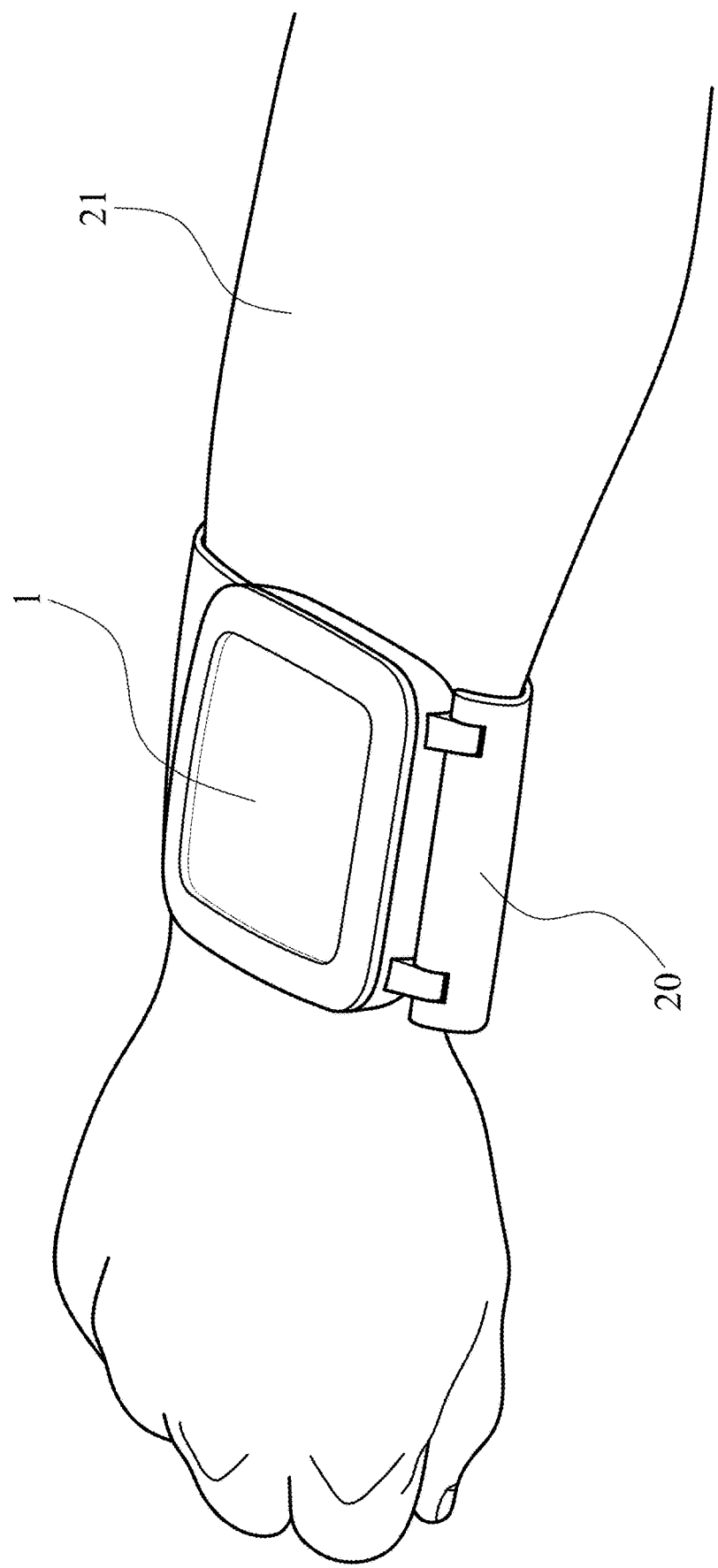
FIG. 2 is a schematic diagram showing a physiological status monitoring apparatus in contact with or worn by a patient according to an embodiment.

FIG. 1 shows one exemplary embodiment of a physiological status monitoring apparatus. As shown in FIG. 1, a physiological status monitoring apparatus 1 is provided. In the embodiment, the physiological status monitoring apparatus 1 operates to monitor breathing status of an object, such as a patient, to generate an index oIndex to indicate the possibility of pauses in breathing during a predetermined time period. In an embodiment, the predetermined time period is the period when the patient is sleeping, and the possibility of pauses in breathing represents a risk level of sleep apnea (particularly, a risk level of obstructive sleep apnea, OSA) during sleeping. As shown in FIG. 1, the physiological status monitoring apparatus 1 comprises a motion sensor 10, a signal pre-processor 11, a feature extractor 12, a memory 13, an event detector 14, an estimator 15, and at least one output device 16. The physiological status monitoring apparatus 1 is a portable device with a healthcare function, such as a wearable device or a smart phone, which can be in contact with or worn by the patient through a band, such as a wrist band or a chest band. For example, as shown in FIG. 2, the physiological status monitoring apparatus 1 is a smart switch worn by the patient through a wrist band 20.

Figure 3:
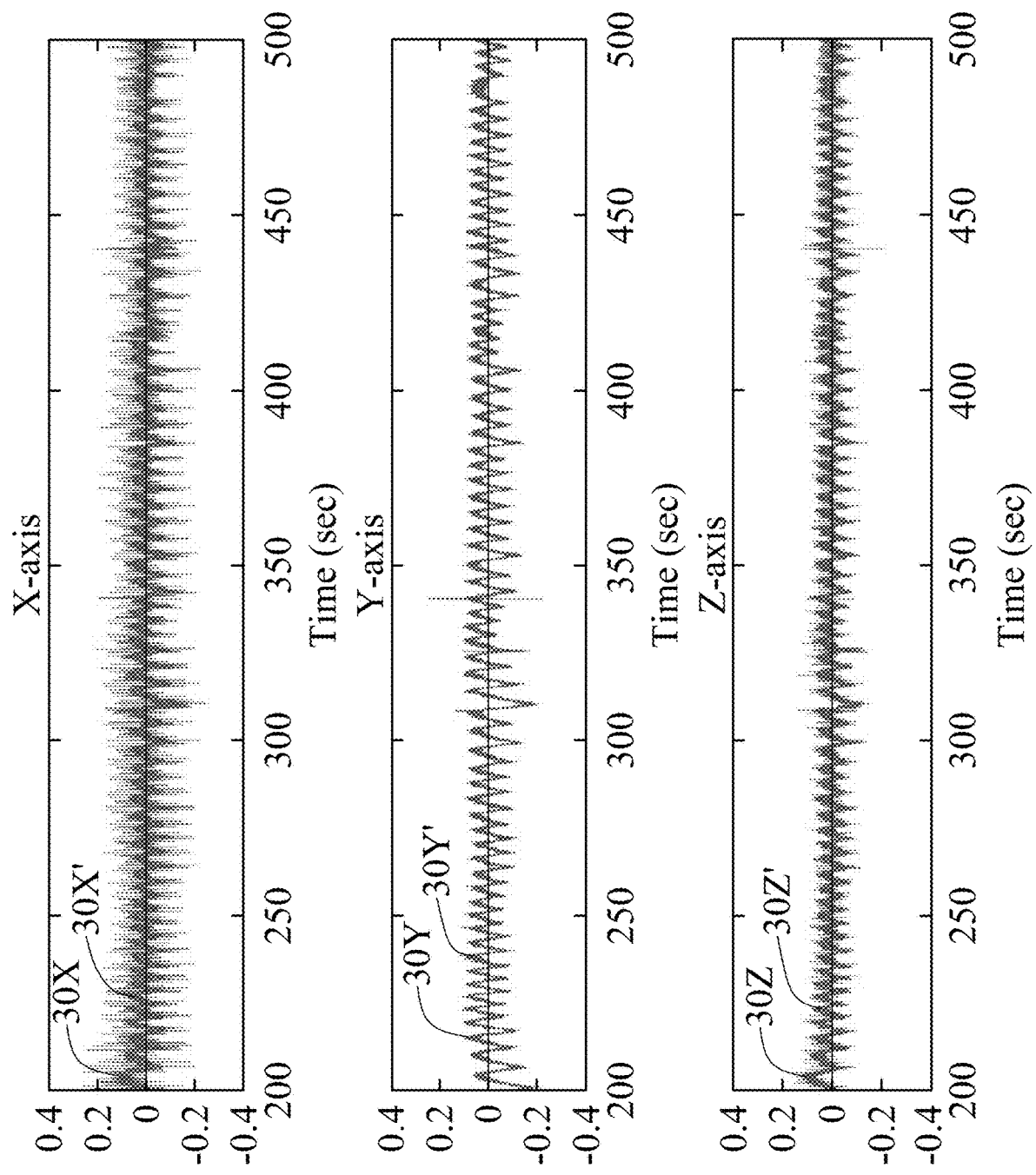
FIG. 3 is a schematic diagram showing an X-axis component, a Y-axis component, and a Z-axis component of a sensing signal in a time-domain generated by a motion sensor according to an embodiment.

In the following paragraphs, the operation of the physiological status monitoring apparatus 1 which is being in contact with or worn by the patient will be described. Referring to FIG. 1, the motion sensor 10 senses the movement of the patient and generates a sensing signal S10 in a time domain according to the sensing result. In an embodiment, the motion sensor 10 is implemented by an accelerometer, and the sensing signal S10 contains at least two direction components. The signal pre-processor 11 comprises a filter 110 and a fluctuation detector 111. The filter 110 receives the sensing signal S10 and performs a filter operation on the sensing signal S10 to generate a filtered sensing signal S10'. In the embodiment, the filter 110 performs the filter operation by removing a direct-current component level from the sensing signal S10 and further filtering high-frequency noise from the sensing signal S10. In an embodiment, as shown in FIG. 3, the sensing signal S10 contains an X-axis component 30X, a Y-axis component 30Y, and a Z-axis component 30Z, wherein the sensing signal S10 shown in FIG. 3 is generated during sleeping. Through the filter operation, a filtered X-axis component 30X', a filtered Y-axis component 30Y', and a filtered Z-axis component 30Z' are generated, and these filtered components 30X', 30Y', and 30Z' form the filtered sensing signal S10' which is a sine wave signal and behaves as a respiratory signal.

Figure 4:
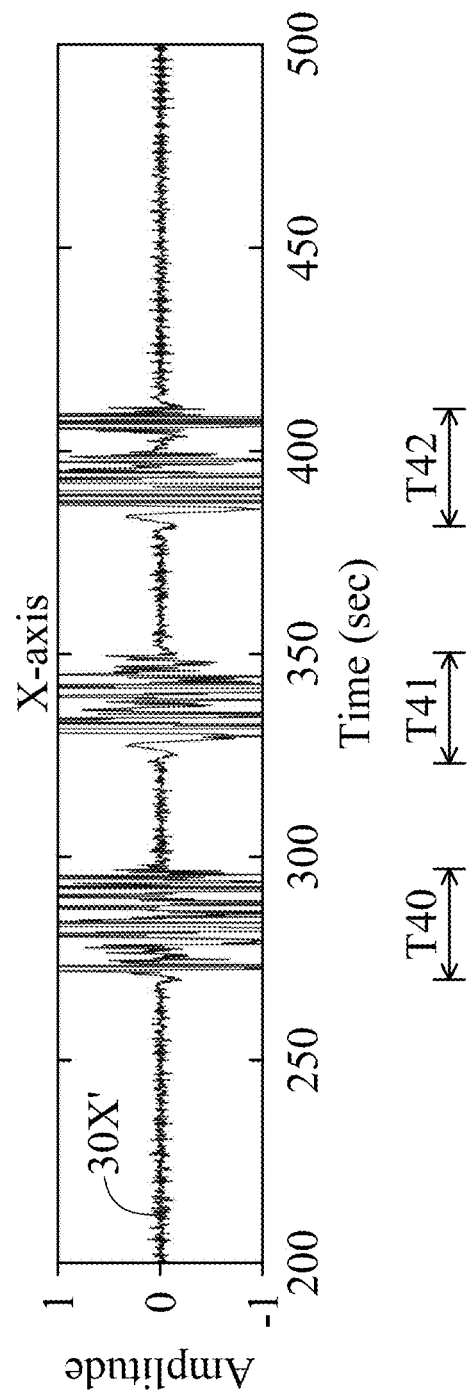
FIG. 4 is a schematic diagram showing large-amplitude fluctuation on an X-axis component of a sensing signal generated by a motion sensor according to an embodiment.

During sleeping, when the patient moves violently, the sensing signal S10 (and also the filtered sensing signal S10') may become excessive great, which affects monitoring results disadvantageously. Thus, according to the embodiment, the fluctuation detector 111 receives the filtered sensing signal S10' and detects whether there is large-amplitude fluctuation on at least one portion of the filtered sensing signal S10'. In response to the detection result, the fluctuation detector 111 outputs a detection signal S111. Referring to FIG. 4, the filtered X-axis component 30X' is shown to explain the operation of the fluctuation detector 111. As shown in FIG. 4, there is large-amplitude fluctuation in the positions of the filtered X-axis component 30X' respectively corresponding to the time periods T40~T42. The detection signal S111 generated by the fluctuation detector 111 indicates the occurrence of the large-amplitude fluctuation in the periods T40~42. In an embodiment, for each filtered component, the fluctuation detector 111 compares the amplitude of the filtered component with a threshold. When the amplitude of the filtered component exceeds the threshold, the fluctuation detector 111 determines that there is large-amplitude fluctuation on a corresponding portion of the filtered component. The fluctuation detector 111 generates the detection signal S111 according to the comparison results related to all the filtered components 30X', 30Y', and 30Z'. In an embodiment, the fluctuation detector 111 may provide the detection signal S111 to the feature extractor 12, and the related description will be shown later.

Figure 5:
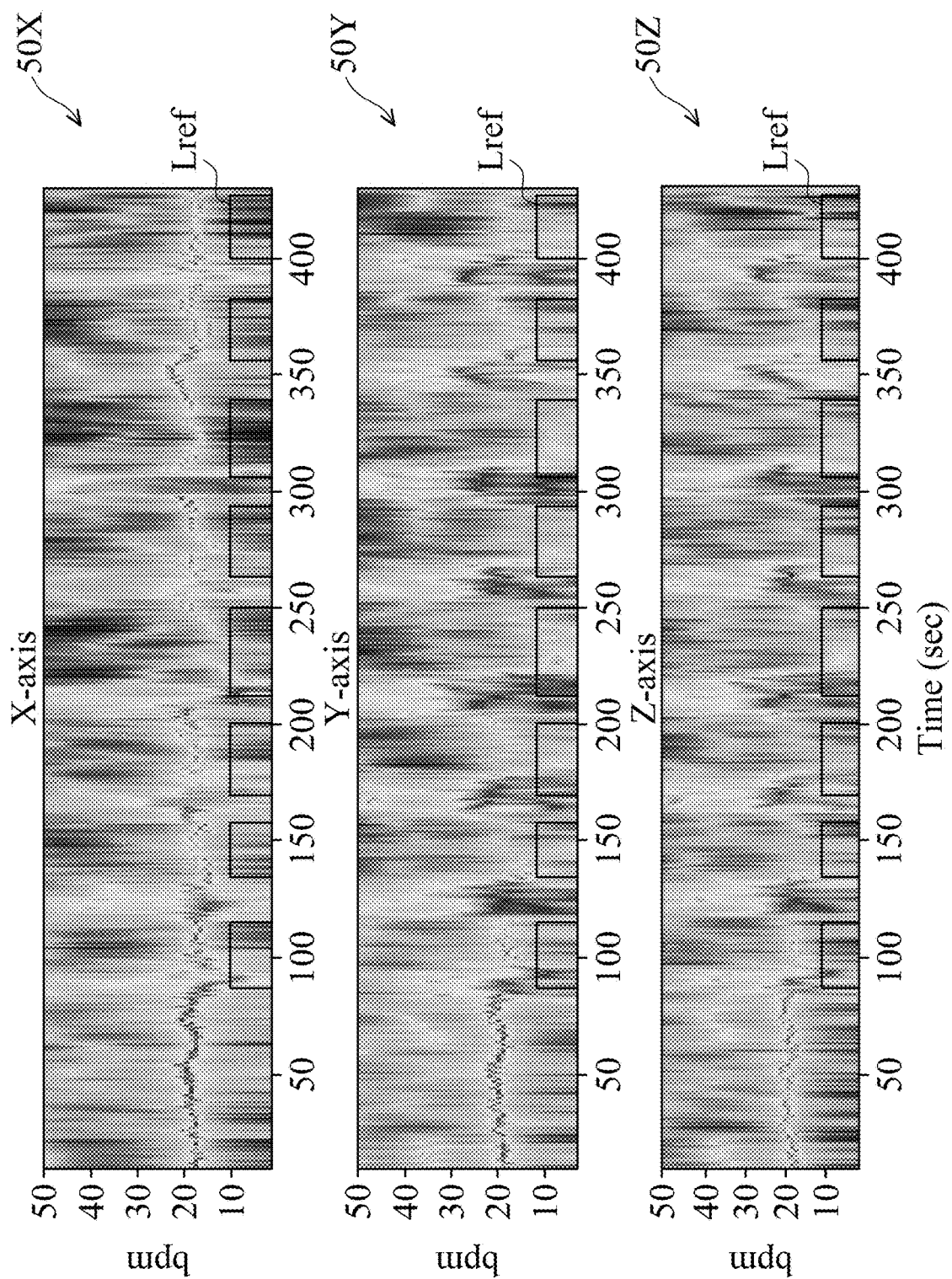
FIG. 5 is a schematic diagram showing an X-axis component, a Y-axis component, and a Z-axis component of a sensing signal in a time-frequency domain generated by a motion sensor according to an embodiment.

The feature extractor 12 also receives the filtered sensing signal S10' and converts the filtered sensing signal S10' from the time domain to a time-frequency domain by a conversion circuit in the feature extractor 12. As shown in FIG. 5, the time-frequency diagram 50X shows the power spectrum density (PSD) on the filtered X-axis component 30X', the time-frequency diagram 50Y shows the PSD on the filtered Y-axis component 30Y', and the time-frequency diagram 50Z shows the PSD on the filtered Z-axis component 30Z'. The value of the PSD is shown in the frequency axis, and the unit of the values of the PSD is bpm (beats per minute). In order to demonstrate the operation of the physiological status monitoring apparatus 1, while the patient is monitored by the physiological status monitoring apparatus 1 during sleeping, medical personnel observe the respiratory status of the patient and make a reference event label each time they find a pause in breathing occurring on the patient, or the patient is further monitored by a sleep apnea monitor device which generates reference event labels indicating OSA events. Referring to FIG. 5, the above reference event labels Lref are shown on the time axes of the time-frequency diagrams 50X, 50Y, and 50Z, and each reference even label spans a time period.

Figure 6:
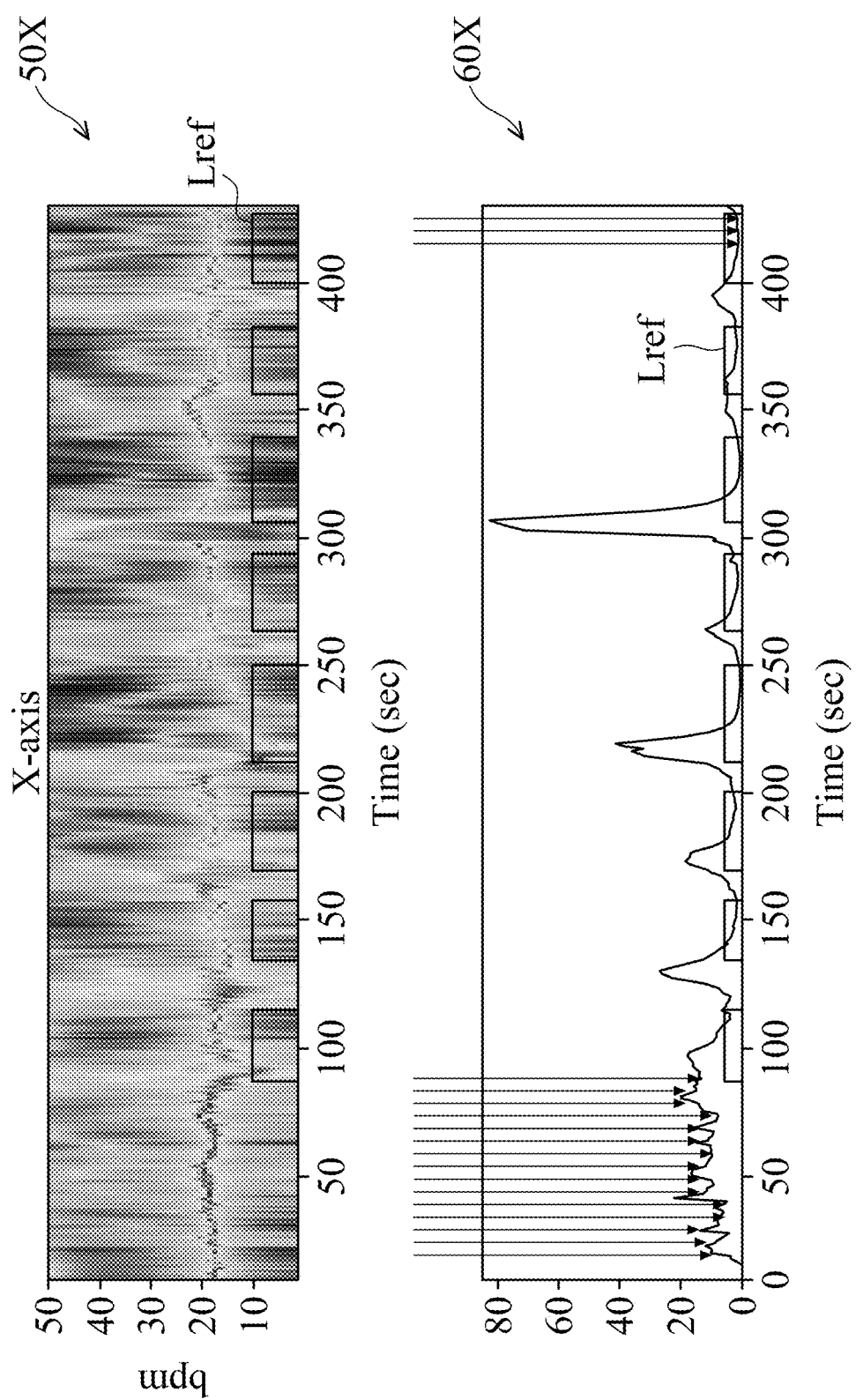
FIG. 6 is a schematic diagram showing calculation of the sums of the power spectrum density (PSD) for an X-axis component of a sensing signal generated by a motion sensor according to an embodiment.

After the domain conversion, for each filtered component, the feature extractor 12 calculates the sum of the values of the PSD in each time point (for example, the sum of the values of the PSD per second in the cases where each time point corresponds to one second) by a calculator in the feature extractor 12. Referring to FIG. 6, the time-frequency diagram 50X for the filtered X-axis component 30X' and a diagram 60X are shown to illustrate the above calculation of the PSD sums. The diagram 60X shows the change in the sums sPSDX of the values of the PSD with time for the filtered X-axis component 30X'. The sums of the values of the PSD on each of the filtered component 30X', 30Y', and 30Z' is calculated as:

$$sPSD(t)=\Sigma_{x=1}^{n}\text{bmp}(t,x) \quad (A)$$

wherein "t" represents timing in seconds, and "n" represents the frequency bandwidth. In the embodiment, for the feature extraction, the range of "t" is from 1 to 450, and "n" is equal to 50. Equation (A) is also represented as:

$$sPSD(t)=\Sigma_{x=1}^{50}\text{bmp}(t,x), t=1,\ldots,450 \quad (B)$$

After the sums sPSDX, sPSDY, and sPSDZ of the values of the PSD respectively on the filtered component 30X', 30Y', and 30Z' are obtained based on Equation (B), the sums sPSDX, sPSDY, and sPSDZ serves as features of the sensing signal S10', and the feature extractor 12 generates feature data D12 containing the sums sPSDX, sPSDY, and sPSDZ. The feature extractor 12 transmits the feature data D12 to the memory 13 for storage. When the feature extractor 12 obtains the sums sPSDX, sPSDY, and sPSDZ for enough seconds, the event detector 14 reads the sums sPSDX, sPSDY, and sPSDZ from the memory 13 and determines whether the sums sPSDX, sPSDY, and sPSDZ in the feature data D12 meet a predetermined criterion. In the following paragraphs, the determination operation will be described by taking the sums sPSDX related to the X-asix component as an example.

Figure 7A:
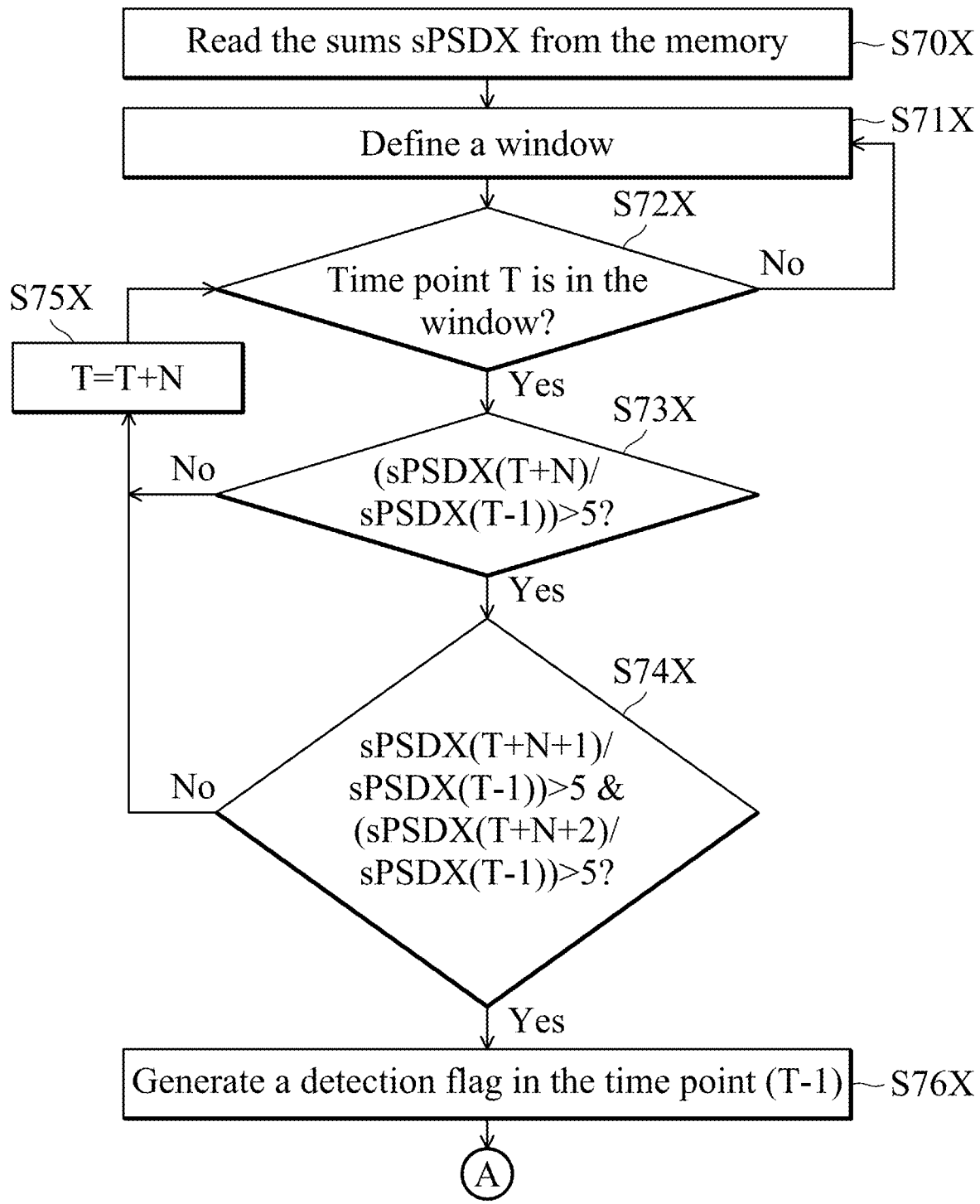
FIGS. 7A-7D show a flow chart of an operation of an event detector according to an embodiment.

FIGS. 7A-7D shows a flow chart of the operation of the event detector 14. Referring to FIG. 7A, when the feature extractor 12 obtains the sums sPSDX for enough seconds, the event detector 14 reads the sums sPSDX from the memory 13 (Step S70X). The event detector 14 defines a window containing a plurality of successive time points (that is, for several seconds) (Step S71X), wherein the number of above successive time points (seconds) is referred to as window size. In the embodiment, the window size is predetermined as 30 seconds. When dealing with one sum sPSDX in the time point T, the event detector 14 determines whether the time point T is in the window (Step S72X). If the time point T is in the window, the process proceeds to Step S73X. At Step S73X, the event detector 14 determines whether the sum sPSDX in the time point (T-1) is relatively small based a predetermined comparison rule, wherein the time point (T-1) occurs before the time point T, and the time points (T-1) and T occur successively (that is, the time points (T-1) and T are two seconds in timing). When determining that the sum sPSDX(T-1) in the time point (T-1) is relatively small, the event detector 14 generates a detection flag in the time point (T-1). In the embodiment, based on the predetermined comparison rule, the event detector 14 determines whether the ratio of the sum sPSDX in the time point (T+N) and the sum sPSDX obtained in the time point (T-1) is larger than 5 (Step S73X: (sPSDX(T+N)/sPSDX(T-1))>5?), wherein the time point (T+N) occurs after the time point T by N seconds). If the ratio of the sum sPSDX in the time point (T+N) and the sum sPSDX obtained in the time point T-1 is larger than 5 (sPSDX(T+N)/sPSDX(T-1))>5, meaning that the sPSDX(T-1) is a smaller value), the process proceeds to Step S74X; if not (sPSDX(T+N)/sPSDX(T-1))≤5), the process proceeds to Step S72X through Step S75X. In Step S75X, the event detector 14 updates T to T+N (T=T+N), and then, at Step S72X, the event detector 14 determines whether the updated time point T is in the window. If the updated time point T is in the window, the process proceeds to Step S73X; if not, the process proceeds to Step S71X to define another 30-second window.

According to the embodiment, the event detector 14 determines whether the sPSDX(T-1) keeps smaller for three seconds. Referring to FIG. 7A, in step S74X, the event detector 14 further determines whether the ratio of the sum sPSDX in the time point (T+N+1) and the sum sPSDX in the time point (T-1) is larger than 5 and whether the ratio of the sum sPSDX in the time point (T+N+2) and the sum sPSDX in the time point (T-1) is also larger than 5 (Step S74X: (sPSDX(T+N+1)/sPSDX(T-1))>5 & (sPSDX(T+N+2)/sPSDX(T-1))>5?), wherein the time points (T+N), (T+N+1), and (T+N+2) occurs successively (that is, the time points (T+N), (T+N+1), and (T+N+2) are three seconds in timing). If the conditions PSDX(T+N+1)/sPSDX(T-1))>5 & (sPSDX(T+N+2)/sPSDX(T-1))>5? are met, the process proceeds to Step S76X; if not, the process proceeds to Step S72X through Step S75X.

Figure 7B:
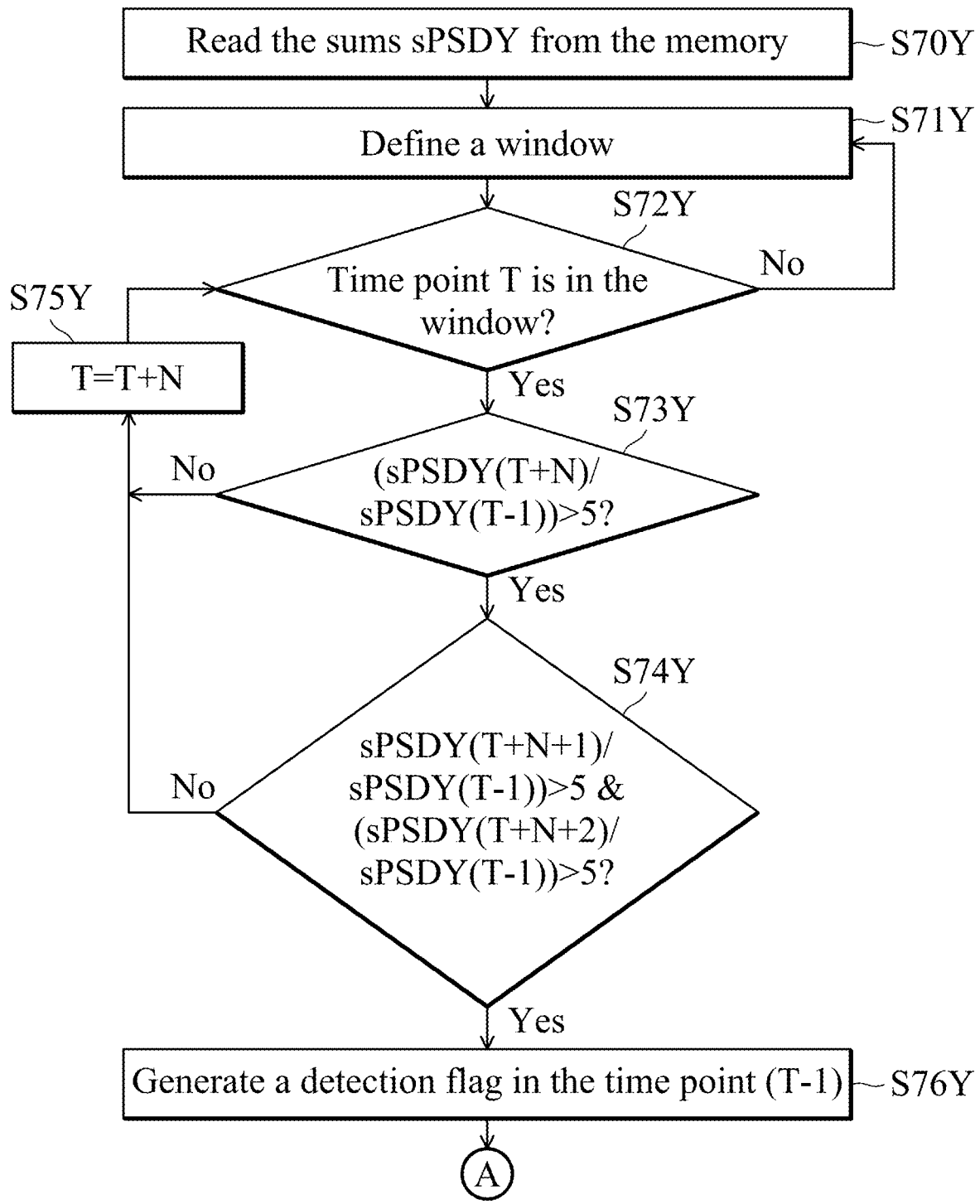
Figure 7C:
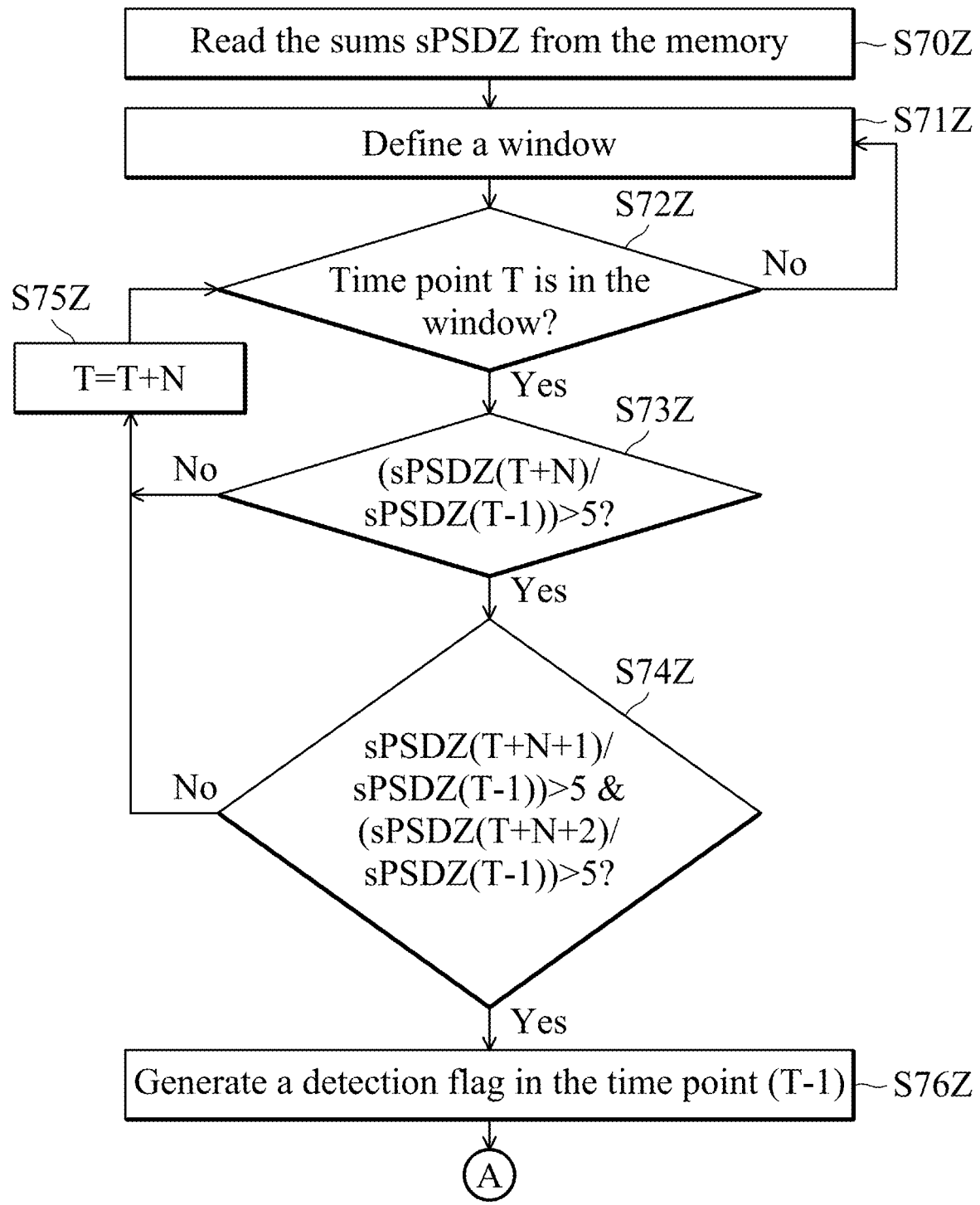
Figure 7D:
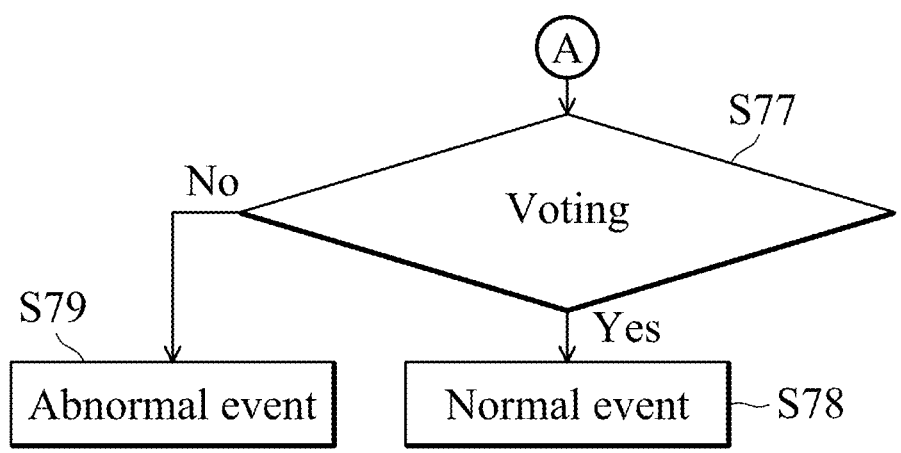
Figure 9:
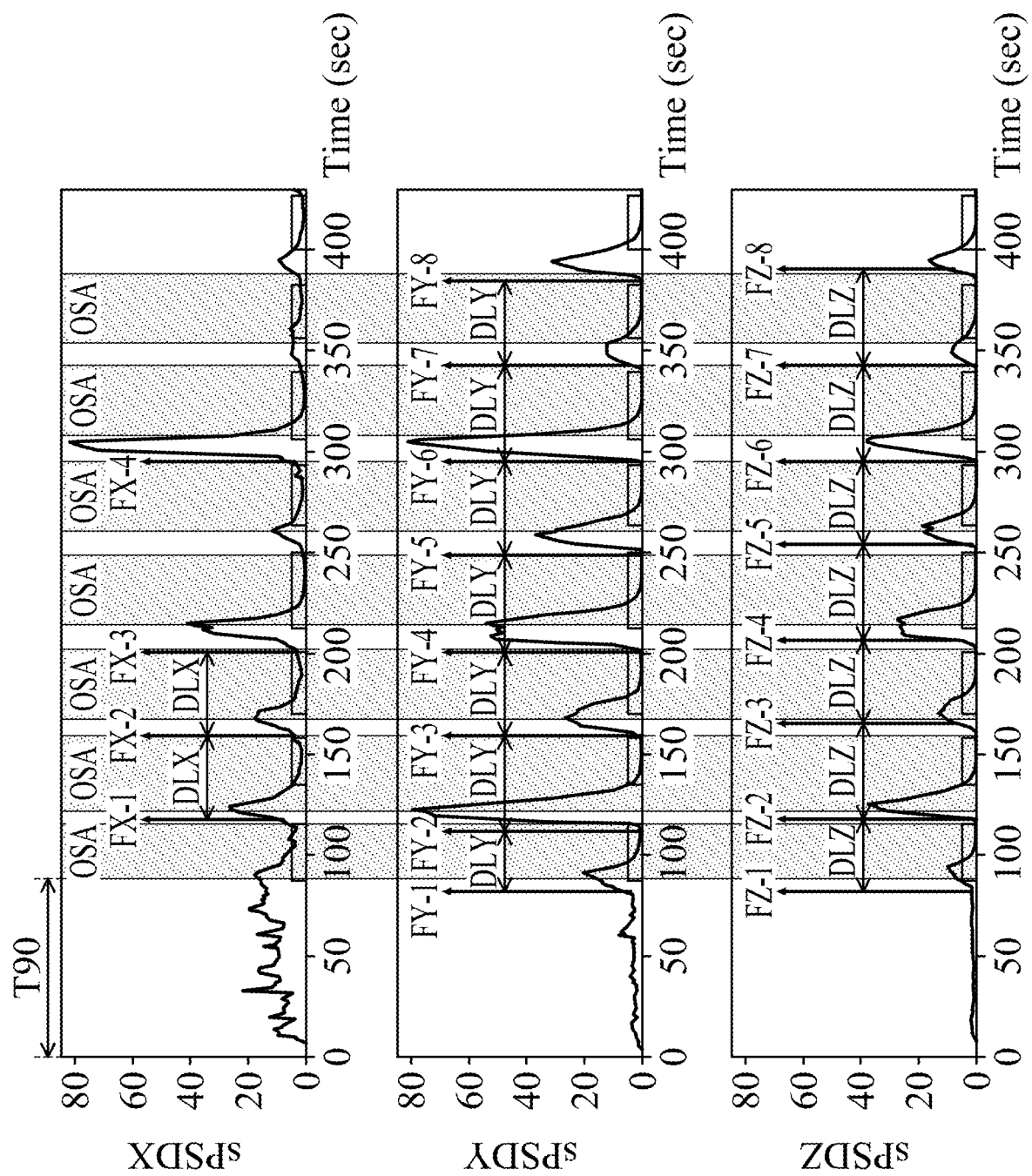
FIG. 9 is a schematic diagram showing event labels for abnormal events according to an embodiment.

In the cases where all the following conditions are met through the determination setps S73X and S74X: sPSDX (T+N)/sPSDX(T-1))>5, sPSDX(T+N+1)/sPSDX(T-1))>5, and (sPSDX(T+N+2)/sPSDX(T-1))>5, the event detector 14 determines that the sum sPSDX in the time point (T-1) is relatively small based the predetermined comparison rule and generates a detection flag for the time point (T-1). Referring to FIGS. 7B and 7C, Steps S70Y~S76Y for the sums sPSDY related the Y-axis component and Steps S70Z~S76Z for the sums sPSDZ related the Z-axis component are similar to Steps S70X~S76X, and the related description is omitted here. Through Steps S70X~S76X, Steps S70Y~S76Y, Steps S70Z~S76Z of FIGS. 7A~7C, detection flags FX-1~FX-4, FY-1~FY-8, and FZ-1~FZ-8 are generated as shown in FIG. 9. Then, referring to FIG. 7D, the process proceeds to Step S77 to perform a voting operation (Step S77: voting). According to the result of the voting operation, the event detector 14 detects at least normal event (Step S78) and/or at least abnormal event (Step S79).

Figure 8:
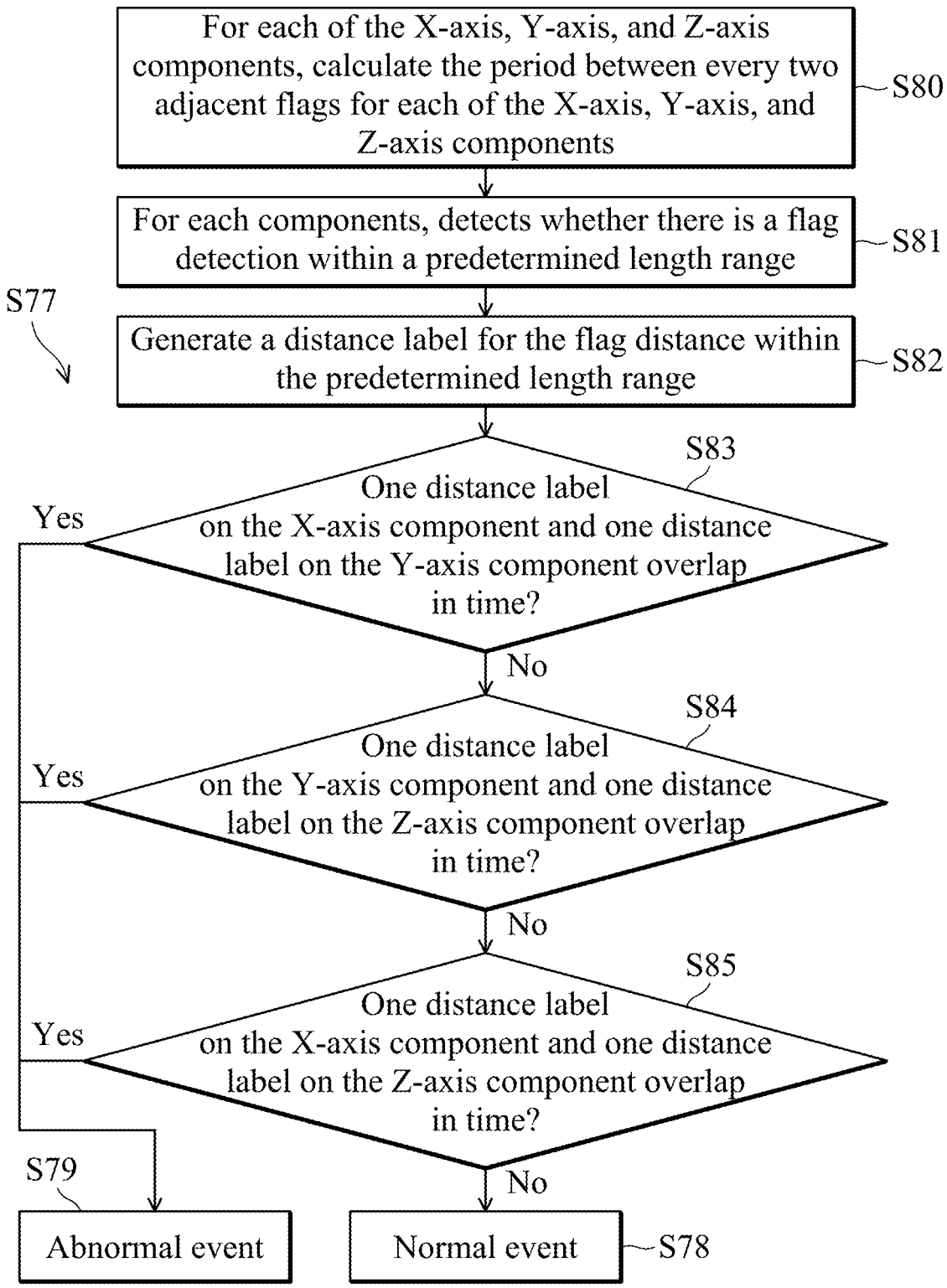
FIG. 8 shows a flow chart of a voting operation according to an embodiment.

FIG. 8 shows a flow chart of the voting operation according to an embodiment. As shown in FIG. 8, after generating the detection flags FX-1~FX-4, FY-1~FY-8, and FZ-1~FZ-8, the event detector 14 calculates the flag distance between every two adjacent flags in time on each of the X-axis, Y-axis, and Z-axis components (Step S80). Then, for each of the X-axis, Y-axis, and Z-axis components, the event detector 14 detects whether there is a flag detection within a predetermined length range (Step S81). In the embodiment, the predetermined length range is greater than ten seconds and less than sixty seconds. When detecting that there is a flag detection within the predetermined length rang, the event detection 14 generates a distance label for this flag distance (Step S82). Referring to FIG. 9, there are two distance labels DLX on the X-axis component, there are seven distance labels DLY on the Y-axis component, and there are seven distance labels DLZ on the Z-axis component. Each distance label spans a time period. After the distance labels are generated, through Steps S83~S85, the event detector 14 determines whether there is a distance label on one component that overlaps with a distance label on another component. Each time the event detector 14 determines that there is one distance label on one component and one distance label on another component overlaps in time, the event detector 14 detects that an abnormal event occurs in the period corresponding to the overlapping distance labels and generates an event label OSA for the abnormal event.

At Step S83, the event detector 14 determines whether one distance label on the X-axis component and one distance label on the Y-axis component overlap in time. Each time the event detector 14 determines that one distance label on the X-axis component and one distance label on the Y-axis component in time, the event detector 14 detects an abnormal event occurring in the period corresponding to the overlapping distance labels (Step S79). If no distance label on the X-axis component overlaps any distance label on the Y-axis component, the process proceeds to Step S84. At Step S84, the event detector 14 determines whether one distance label on the Y-axis component and one distance label on the Z-axis component overlap in time. Each time the event detector 14 determines that one distance label on the Y-axis component and one distance label on the Z-axis component in time, the event detector 14 detects an abnormal event occurring in the period corresponding to the overlapping distance labels (Step S79). If no distance label on the Y-axis component overlaps any distance label on the Z-axis component, the process proceeds to Step S85. At Step S85, the event detector 14 determines whether one distance label on the X-axis component and one distance label on the Z-axis component overlap in time. Each time the event detector 14 determines that one distance label on the X-axis component and one distance label on the Z-axis component in time, the event detector 14 detects an abnormal event occurring in the period corresponding to the overlapping distance labels (Step S79). If no distance label on the X-axis component overlaps any distance label on the Z-axis component, the process proceeds to Step S78. In Step S78, the event detector 14 detects a normal event. As shown in FIG. 9, there are seven abnormal events represented by the event labels OSA. In the period T90, there is no detection flag and no event label. Thus, the normal event detected by the event detector 14 occurs in the period T90. Referring to FIG. 9, the time periods of the event labels OSA matches the time period of the reference event labels Lref. Thus, through the above operations, the physiological status monitoring apparatus 1 can accurately determine when the OSA events occur.

According to the above description, the fluctuation detector 111 can output the detection signal S111. In an embodiment, the feature extractor 12 receives the detection signal S111 to obtain the occurrence of the large-amplitude fluctuation on each of the filtered components 30X', 30Y', and 30Z'. Then, for each of the filtered components 30X', 30Y', and 30Z', the feature extractor 12 calculates the sums sPSDX, sPSDY, and sPSDZ without using the portions of the filtered components 30X', 30Y', and 30Z' corresponding to the occurrence of the large-amplitude fluctuation. Accordingly, the event detector 14 detects the occurrence of the abnormal events according to the sums sPSDX, sPSDY, and sPSDZ which are derived from the remaining portions of the filtered components 30X', 30Y', and 30Z', which increases the accuracy of the detection operation of the event detector 14.

In the embodiment, the event detector 14 further counts the number Nsleep of abnormal events which occur in the predetermined time period (that is, during sleeping) and generates event label data D14 according to the result of the detection of the abnormal events and the counted number of abnormal events. Thus, the event label data D14 may contain information about, for example, the time when the abnormal events occur and/or the number of abnormal events which occur in the predetermined time period.

The estimator 15 receives the event label data D14 to obtain the number Nsleep of abnormal events which occur during sleeping and generates the index oIndex according to the obtained number Nsleep according to the following equation:

$$oIndex = \frac{Nsleep \times 60}{Tsleep} \quad (C)$$

wherein, Tsleep represents the time when the patient is sleeping in minutes. The index oIndex represents a risk level of OSA. Moreover, the estimator 15 determines the severity degree of OSA by determining the value of the index oIndex. Referring to Table 1, when the value of the index oIndex is smaller than 5 (oIndex<5), the estimator 15 determines that the severity degree of OSA is low or the breathing is normal; when the value of the index oIndex is in the range from 5 to 30 (5≤oIndex≤30), the estimator 15 determines that the severity degree of OSA is middle, when the value of the index oIndex is greater than 30 (oIndex>30), the estimator 15 determines that the severity degree of OSA is high. The extractor 15 generates an alarm signal S15A according to the determination of the severity degree of OSA.

TABLE 1

| Severity degree | Index | Color of alarm message |
|---|---|---|
| Low | oIndex < 5 | Green |
| Middle | (5 ≤ oIndex ≤ 30 | Yellw |
| High | oIndex > 30 | Red |

Referring to FIG. 1, the at least one output device 16 of the physiological status monitoring apparatus 1 comprises a displayer 160. The displayer 160 can receive the event label data D14 from the event detector 14 and, according to the information contained in the event label data D14, show values, diagrams, or text messages related to the time when the abnormal events occur or the number of abnormal events which occur during sleeping. The displayer 160 also receives the index oIndex from the estimator 15 and shows the index oIndex on the screen. In an embodiment, the displayer 160 may receive the alarm signal S15A from the estimator 15 and show an alarm message by different colors which are determined according the determined severity degree of OSA, as shown in Table 1.

In another embodiment, the at least one output device 16 may further comprise an output device 161 which communicates with at least one of the event detector 14 and the estimator 15 by a wire or wireless manner to receive at least one of the event label data D14, the index oIndex, and an alarm signal S15A. The output device 161 may be a healthcare monitoring device, a speaker, or a smart phone. According to at least one of the event label data D14, the index oIndex, and an alarm signal S15A, the output device 161 can show information related to the occurrence of the abnormal events, show the index oIndex, and/or show (or play) an alarm message.

In an embodiment, referring to FIG. 1, a photoplethysmogram (PPG) sensor 17 communicates with the physiological status monitoring apparatus 1 by a wire or wireless manner. When the PPG sensor 17 is activated, it operates to sense pulses of a blood vessel of the patient to generate a bio-signal S17. The bio-signal S17 contains information about the heart rate and oxyhemoglobin saturation (SPO2) which are highly correlated with occurrence of OSA. The PPG sensor 17 may provide the bio-signal S17 to the estimator 15. Thus, the estimator 15 determines the severity degree of OSA according to not only the value of the index oIndex but also the bio-signal S17.

The PPG sensor 17 may be controlled by at least one of the event detector 14 and the estimator 15. In an embodiment, the event detector 14 counts the number of abnormal events during the sleeping and determines whether the counted number of abnormal events exceeds an upper threshold. When determining that the counted number of abnormal events exceeds an upper threshold, the event detector 14 generates an enable signal S14 to activate the PPG sensor 17. In another embodiment, the estimator 15 determines whether the value of the index oIndex exceeds a threshold value. When determining that the value of the index oIndex exceeds the threshold value, the estimator 15 generates an enable signal S15B to activate the PPG sensor 17. According to the above embodiments, the PPG sensor 17 is not activated continuously, which decrease the power consumption.

In another embodiment, another bio-signal sensor 18 communicates with the physiological status monitoring apparatus 1 by a wire or wireless manner. The bio-signal sensor 18 operates to sense other physiological features of the patient and generates a bio-signal S18 to the estimator 15. For example, the bio-signal sensor 18 is an ExG monitor used to monitor at least one of electrocardiography (ECG), electroencephalograph (EEG), electromyography (EMG), electrooculography (EOG), electroretinogram (ERG), electrogastrography (EGG), and electroneurogram (ENG) of the patient. In this embodiment, the estimator 15 determines the severity degree of OSA according to not only the value of the index oIndex but also the bio-signal S18.

In an embodiment, a light detector 19 communicated with the physiological status monitoring apparatus 1 by a wire or wireless manner. The light detector 19 operates to sense the intensity of the ambient light and generate a detection signal S19 in response to the detection result. The event detector 14 receives the detection signal S19 to obtain the intensity of the ambient light and determines when the predetermined time period (that is the period when the patient is sleeping) occurs according to the intensity of the ambient light, so that the event detector 14 can count the number of abnormal events which occur in the predetermined time period. In the above embodiments, the physiological status monitoring apparatus 1, the PPG sensor 17, the bio-signal sensor 18, and the light detector 18 form a physiological status monitoring system 2.

According to the above embodiments, the physiological status monitoring apparatus 1 can monitor breathing status of the patient by using only one sensor (the motion sensor 10), which simplifies the design of the physiological status monitoring apparatus 1 and avoids the problem of low signal quality induced from poor contacting with the patient. Thus, the index generated according to the detection of the patient's motion can accurately indicate the risk level of OSA.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A physiological status monitoring apparatus comprising:
   a motion sensor configured to sense movement of an object to generate a sensing signal;
   an event detector configured to detect abnormal events occurring on the object according to the sensing signal;
   an estimator configured to output an index according to at least one abnormal event which occurs during a predetermined time period to indicate a possibility of pauses in breathing; and
   a feature extractor receiving the sensing signal and extracting features of the sensing signal in a time-frequency domain to generate feature data,
   wherein the event detector receives the feature data and determines whether the feature data meets a predetermined criterion, and
   wherein each time the event detector determines that the feature data meets the predetermined criterion, the event detector detects one abnormal event and generates an event label for the one abnormal event, and
   wherein the event detector outputs event label data in response to a result of the detection of the abnormal events.

2. The physiological status monitoring apparatus as claimed in claim 1,
   wherein the sensing signal comprises three signal components, and the feature extractor converts the sensing signal from a time domain to the time-frequency domain,
   wherein, for each signal component, the feature extractor calculates a sum of all power spectrum density (PSD) values for each time point, and the calculated sums of the three signal components serve as the features of the sensing signal,
   wherein, for each signal component, the event detector receives the feature data and determines whether the calculated sum for one time point is smaller than a predetermined amount based a predetermined comparison rule according to the feature data and, in response to determining that the calculated sum for the one time point is smaller than the predetermined amount, generates a detection flag in the one time point;
   wherein, for each signal component, the event detector determines whether there is a flag distance between every two adjacent flags within a predetermined length range,
   wherein in response to determining that there is one flag distance within the predetermined length range, the event detector generates a distance label for the one flag distance,
   wherein the event detector determines whether there is one distance label on one of the signal components and one distance label on another of the signal components overlaps in time, and
   wherein in response to determining that there is one distance label on one of the signal components and one distance label on another of the signal components overlaps, the event detector detects one abnormal event and generates one event label for the one abnormal event.

3. The physiological status monitoring apparatus as claimed in claim 1, wherein the estimator receives the event label data, obtains the number of abnormal events which occur during the predetermined time period according to the event label data, and generates the index according to the obtained number of abnormal events.

4. The physiological status monitoring apparatus as claimed in claim 1, wherein the possibility of pauses in breathing represents a risk level of sleep apnea.

5. The physiological status monitoring apparatus as claimed in claim 1, further comprising:
   a signal pre-processor configured to receive the sensing signal, filter a direct-current component level and high-frequency noise from the sensing signal, and detect whether there is amplitude fluctuation that exceeds a predetermined amount on at least one portion of the sensing signal,
   wherein in response to detecting that there is an amplitude fluctuation exceeding the predetermined amount on at least one portion of the sensing signal, the event detector detects that the abnormal events occurring on the object according to the remaining portions of the sensing signal.

6. The physiological status monitoring apparatus as claimed in claim 1, further comprising:
   a photoplethysmogram (PPG) sensor configured to sense pulses of a blood vessel of the object to generate a bio-signal when the PPG is activated,
   wherein the estimator is configured to output the index according to the least one abnormal event which occurs during the predetermined time period and the bio-signal.

7. The physiological status monitoring apparatus as claimed in claim 6,
   wherein the event detector counts the number of abnormal events which occur during the predetermined time period and determines whether the counted number of abnormal events exceeds an upper threshold, and
   wherein in response to the estimator determining that the counted number of abnormal events exceeds the upper threshold, the event detector outputs an enable signal to activate the PPG sensor.

8. A physiological status monitoring apparatus comprising:
   a motion sensor configured to sense movement of an object to generate a sensing signal;
   an event detector configured to detect abnormal events occurring on the object according to the sensing signal;
   an estimator configured to output an index according to at least one abnormal event which occurs during a predetermined time period to indicate a possibility of pauses in breathing; and
   an output device coupled to the estimator and configured to receive the index,
   wherein the output device shows a value, a diagram or a text message related to the possibility of pauses in breathing.

9. A physiological status monitoring apparatus comprising:
   a motion sensor configured to sense movement of an object to generate a sensing signal;
   an event detector configured to detect abnormal events occurring on the object according to the sensing signal;
   an estimator configured to output an index according to at least one abnormal event which occurs during a predetermined time period to indicate a possibility of pauses in breathing; and a bio-signal sensor coupled to the estimator,
wherein the estimator determines whether a value of the index exceeds a threshold value, and
wherein in response to the estimator determining whether the value of the index exceeds the threshold value, the estimator outputs an enable signal to activate the bio-signal sensor to sense physiological feature of the object.

\* \* \* \* \*